(12) United States Patent
Toomey et al.

(10) Patent No.: US 9,750,532 B2
(45) Date of Patent: Sep. 5, 2017

(54) ACCESS NEEDLES AND STYLET ASSEMBLIES

(71) Applicant: Cook Medical Technologies LLC, Bloomington, IN (US)

(72) Inventors: Ciarán Toomey, Co. Cork (IE); Michael Dunning, Co. Westmeath (IE); Fionan Keady, Co. Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 259 days.

(21) Appl. No.: 14/277,496

(22) Filed: May 14, 2014

(65) Prior Publication Data

US 2014/0357983 A1   Dec. 4, 2014

Related U.S. Application Data

(60) Provisional application No. 61/829,421, filed on May 31, 2013.

(51) Int. Cl.
*A61B 17/34* (2006.01)
*A61B 6/12* (2006.01)
(Continued)

(52) U.S. Cl.
CPC .......... *A61B 17/3478* (2013.01); *A61B 1/018* (2013.01); *A61B 6/12* (2013.01);
(Continued)

(58) Field of Classification Search
CPC .......... A61M 25/0612; A61M 25/0693; A61M 5/427; A61M 2025/0915;
(Continued)

(56) References Cited

U.S. PATENT DOCUMENTS 4,582,061 A    4/1986 Fry
4,869,259 A    9/1989 Elkins
(Continued)

FOREIGN PATENT DOCUMENTS

EP        0904797 A2   3/1999
WO        WO 96/13295  5/1996
(Continued)

OTHER PUBLICATIONS

PCT International Search Report dated Oct. 13, 2014 for International Application No. PCT/US2014/037992.

*Primary Examiner* — Elmer Chao
(74) *Attorney, Agent, or Firm* — Brinks Gilson & Lione (57) ABSTRACT

Access needles and methods of using the needles are set forth in this disclosure. The needles can include a handle and a cannula having a proximal end operatively connected to the handle, a distal end, and a lumen extending through the body of the cannula. A protective sheath may surround the cannula. Further, a stylet may be removably disposed within the lumen of the cannula. The stylet includes a piercing tip at a distal end and a flexible body length extending proximally from the piercing tip to the handle. The flexible body of the stylet provides a path of fluid communication through the lumen of the cannula such that a contrast fluid can effectively pass through the lumen of the cannula. Methods of introducing cannulas to target locations within a body of a patient are also set forth in this disclosure.

18 Claims, 4 Drawing Sheets

(51) Int. Cl.
  *A61B 8/08* (2006.01)
  *A61B 17/00* (2006.01)
  *A61B 1/018* (2006.01)
  *A61B 10/02* (2006.01)
  *A61B 10/04* (2006.01)
  *A61B 90/00* (2016.01)

(52) U.S. Cl.
  CPC ............ *A61B 8/0841* (2013.01); *A61B 8/481* (2013.01); *A61B 17/00234* (2013.01); *A61B 17/3417* (2013.01); *A61B 10/0233* (2013.01); *A61B 17/3403* (2013.01); *A61B 2010/045* (2013.01); *A61B 2017/0034* (2013.01); *A61B 2017/00292* (2013.01); *A61B 2017/00336* (2013.01); *A61B 2017/3413* (2013.01); *A61B 2090/3925* (2016.02)

(58) Field of Classification Search
  CPC ......... A61M 2025/09175; A61M 2025/09191; A61B 5/06; A61B 5/0059; A61B 17/3403; A61B 2090/3945; A61B 2019/5445
  See application file for complete search history.

(56) References Cited

U.S. PATENT DOCUMENTS

| | | | |
|---|---|---|---|
| 4,977,897 A | 12/1990 | Hurwitz | |
| 4,986,279 A * | 1/1991 | O'Neill | 600/567 |
| 5,357,961 A | 10/1994 | Fields et al. | |
| 5,490,521 A | 2/1996 | Davis et al. | |
| 5,964,727 A | 10/1999 | Edwards et al. | |
| 6,018,676 A | 1/2000 | David et al. | |
| 6,053,870 A | 4/2000 | Fulton, III | |
| 6,273,861 B1 | 8/2001 | Bates et al. | |
| 6,306,094 B1 | 10/2001 | Joseph | |
| 6,530,933 B1 | 3/2003 | Yeung et al. | |
| 6,607,496 B1 | 8/2003 | Poor et al. | |
| 6,610,016 B1 | 8/2003 | Violante et al. | |
| 6,663,645 B2 * | 12/2003 | Nishtala | A61B 17/32056 600/567 |
| 6,852,091 B2 * | 2/2005 | Edwards | A61B 18/00 604/22 |
| 6,860,856 B2 | 3/2005 | Ward et al. | |
| 6,871,086 B2 | 3/2005 | Nevo et al. | |
| 6,895,282 B2 | 5/2005 | Gellman et al. | |
| 6,936,048 B2 | 8/2005 | Hurst | |
| 6,962,588 B2 | 11/2005 | Sauvageau et al. | |
| 6,976,955 B2 | 12/2005 | Hardin et al. | |
| 7,087,212 B2 | 8/2006 | Cantrell et al. | |
| 7,204,826 B2 | 4/2007 | Tremaglio et al. | |
| 7,241,736 B2 | 7/2007 | Hunter et al. | |
| 7,335,155 B2 | 2/2008 | Chu | |
| 7,713,215 B2 | 5/2010 | Shriver | |
| 2002/0173719 A1 | 11/2002 | Zhao et al. | |
| 2003/0073902 A1 | 4/2003 | Hauschild et al. | |
| 2003/0130575 A1 | 7/2003 | Desai | |
| 2003/0158480 A1 | 8/2003 | Tornes et al. | |
| 2004/0002647 A1 | 1/2004 | Desai | |
| 2004/0162559 A1 * | 8/2004 | Arramon | A61B 17/3417 606/62 |
| 2005/0165467 A1 | 7/2005 | Hunter et al. | |
| 2005/0182297 A1 * | 8/2005 | Gravenstein | A61B 1/0017 600/139 |
| 2005/0256426 A1 | 11/2005 | Brugge | |
| 2005/0261571 A1 | 11/2005 | Willis et al. | |
| 2006/0235446 A1 | 10/2006 | Godin | |
| 2006/0247530 A1 | 11/2006 | Hardin, Jr. et al. | |
| 2007/0021767 A1 | 1/2007 | Breznock | |
| 2007/0088247 A1 | 4/2007 | Bliweis et al. | |
| 2008/0097213 A1 | 4/2008 | Carlson et al. | |
| 2008/0161843 A1 * | 7/2008 | Clague | A61B 17/00008 606/167 |
| 2010/0160731 A1 * | 6/2010 | Giovannini | A61B 17/3478 600/117 |
| 2010/0317963 A1 | 12/2010 | Clancy | |

FOREIGN PATENT DOCUMENTS

| | | |
|---|---|---|
| WO | WO 96/27329 | 9/1996 |
| WO | WO 02/078611 A2 | 10/2002 |
| WO | WO 2007/067324 A1 | 6/2007 |
| WO | WO 2007/070374 A2 | 6/2007 |
| WO | WO 2008/062451 A2 | 5/2008 |

* cited by examiner

ACCESS NEEDLES AND STYLET ASSEMBLIES

CROSS-REFERENCE TO RELATED APPLICATIONS

This application claims priority to U.S. Provisional Application Ser. No. 61/829,421, filed May 31, 2013, the disclosure of which is incorporated herein by reference in its entirety.

BACKGROUND OF THE INVENTION

1. Field of the Invention

The present disclosure relates generally to medical devices. More particularly, the present disclosure relates to access needles having distinctly configured stylets that allow for the passage of contrast fluid.

2. Description of the Related Art

The development of minimally invasive methods and devices over recent years has revolutionized the practice of medicine. These methods and devices allow medical professionals to perform a wide variety of procedures while minimizing trauma to the patient. Access needles are used in connection with certain minimally invasive medical procedures. These needles can include a tubular cannula body that can form a conduit between a target site within the body of a patient and a location outside of the patient's body. This conduit can subsequently be used by a medical professional for performing certain procedures in connection with the target site or for running a wire guide therethrough.

An access needle can include a stylet in the lumen of its cannula to avoid inadvertent sample collection at the distal end of the cannula, to provide a sharp tip capable of making a puncture, and to provide some reinforcement to the cannula as it travels to the target site within the body. After the distal end of the needle arrives at its target location within the body, the stylet can be withdrawn, thereby clearing a space through the cannula lumen where, for example, a wire guide may be placed. A medical professional performing such a procedure must be able to determine the exact location of the distal end of the cannula to be sure that it has arrived at the precise target site within the body of the patient.

One method useful for determining the location of the distal end of the cannula within the patient's body is carried out using endoscopic ultrasound (EUS). EUS provides a medical professional with the ability to visualize the location of the distal end of the needle within the patient's body without requiring an open incision, use of large-bore needles, or percutaneous trocars. If this method is used for location purposes, the access needle may comprise an echogenic tip at its distal end. Ideally, EUS can then be used to determine the location of the echogenic tip. However, EUS technology is not always capable of providing the medical professional with precise location data. Thus, it could be advantageous to couple EUS with a different form of location technology either to supplement the EUS data or provide location data in the event that EUS is unsuccessful.

In this regard, fluoroscopy may be used as an additional method to determine the location of the distal end of a needle within a patient's body. In one aspect, fluoroscopy can be used to detect a dye or contrast fluid that has been placed within the patient's body. Specifically, x-rays are emitted through the body of the patient to determine the exact location of the contrast fluid. The resulting image can be transmitted to a monitor and a medical professional carrying out the procedure can then determine if the distal end of the needle is at the target site.

When using this form of location technology, one must be able to supply a radio-opaque dye (e.g. contrast fluid) through the lumen of the cannula and out its distal end. This can be problematic, especially when a stylet is located within the lumen of the cannula. Most prior art stylets are formed of a solid wire and substantially occupy the entire inner diameter of the lumen. As such, they would effectively block or seriously impede the flow of contrast fluid through the cannula lumen. It is thus desirable to provide stylet configurations that will allow for the passage of contrast fluid through the lumen of the cannula without having to provide a larger cannula and/or additional lumen(s).

BRIEF SUMMARY OF THE INVENTION

Access needles are disclosed herein. In one aspect, the access needle comprises an elongate hollow cannula having a proximal end, a distal end, and a lumen extending therebetween; and a stylet removably disposed within the lumen of the cannula, the stylet comprising a piercing tip at a distal end of the stylet; and a flexible body length extending proximally from the piercing tip toward the proximal end, whereby the flexible body of the stylet provides a path of fluid communication through the entire lumen of the cannula such that a contrast fluid can effectively pass through the lumen of the cannula.

In another aspect, the access needle comprises an elongate hollow cannula having a proximal end, a distal end, and a lumen extending therebetween; and a stylet removably disposed within the lumen of the cannula, the stylet comprising a piercing tip at a distal end of the stylet; and a flexible body length extending proximally from the piercing tip toward the proximal end, whereby the flexible body of the stylet provides a path of fluid communication through the entire lumen of the cannula such that a contrast fluid can effectively pass through the lumen of the cannula, wherein the stylet comprises a coiled wire and a distal end of the coiled wire is connected to a proximal end of the piercing tip.

In an additional aspect, the access needle comprises an elongate hollow cannula having a proximal end, a distal end, and a lumen extending therebetween; and a stylet removably disposed within the lumen of the cannula, the stylet comprising a piercing tip at a distal end of the stylet; and a flexible body length extending proximally from the piercing tip toward the proximal end, whereby the flexible body of the stylet provides a path of fluid communication through the entire lumen of the cannula such that a contrast fluid can effectively pass through the lumen of the cannula, wherein the stylet comprises a plurality of wire strands and a distal end of each wire strand comprising the plurality of wire strands is connected to a proximal end of the piercing tip.

Methods of introducing a cannula to a target location within a body of a patient through an endoscope are also disclosed. In one aspect, the method comprises providing any of the aforementioned access needles; loading the distal end of the cannula and stylet into a lumen of the endoscope; puncturing the target location with the piercing tip, the distal end of the cannula, and the distal end of the stylet; directing contrast fluid to flow through the cannula lumen and exit the distal end of the cannula; fluoroscopically visualizing the body of the patient to determine a location of the contrast fluid; confirming by the location of the contrast fluid that the distal end of the cannula is at the target location; withdrawing the stylet; and leaving the cannula in place with the distal end of the cannula at the target location.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

As will be more fully described hereinafter, the present disclosure relates to access needles and distinctly configured stylets. Although the stylets are described in connection with access needles, the present disclosure is intended to cover the use of the presently disclosed stylets in connection with other medical devices, such as standard EUS needles and percutaneous needles. Unless otherwise defined, all technical and scientific terms used herein have the same meaning as commonly understood to one of ordinary skill in the art to which this disclosure pertains. In case of conflict, the present document, including definitions, will control. Preferred systems, components, methods, and materials are described below, although systems, methods, components, and materials similar or equivalent to those described herein can be used in the practice or testing of the present disclosure. The systems, components, materials, methods, and examples disclosed herein are illustrative only and not intended to be limiting.

In the present disclosure, the terms "proximal" and "distal" will be used to describe the opposing axial ends of particular components of the medical devices disclosed herein, including the various components of the access needles described herein. The term "proximal" is used in its conventional sense to refer to the end of the apparatus (or component thereof) that is closest to the operator or medical professional during use of the apparatus. The term "distal" is used in its conventional sense to refer to the end of the apparatus (or component thereof) that is initially inserted into the body of the patient, or that is furthest from the operator or medical professional using the device.

As used herein, the term "echogenic" is defined as a component having enhanced echogenicity. Specifically, it is used to refer to materials or portions of materials that are constructed or are treated to have greater reflectivity of ultrasonic waves than standard materials used for a cannula, a cannula, and/or a stylet. It is known in the art that most materials used for a cannula, cannula, and/or stylet will reflect some ultrasonic waves, but the term "echogenicity," as used herein, includes treating the surface with dimples, divots, or the like, (and/or, when specifically referenced, using a material known to provide an enhanced echogenic profile) configured to provide clear ultrasound visualization at a resolution providing for accurate location and navigation of a device in the body of a patient.

The term "cannula" recited herein is defined to include tubular bodies that may be rigid or flexible. The bodies have a generally tubular or a substantially tubular wall defining a lumen. The term "cannula" is also intended to cover needles (e.g. medical devices having a tip configured to penetrate or otherwise pass through tissue), as well as catheters having a lumen through which structures and/or materials may be directed. Such needles and catheters may comprise polymeric, metallic, and/or plastic materials. In many of the aspects disclosed herein, the access needle includes a flexible cannula combined with a stylet.

The term "catheter" recited herein is intended to cover any catheter known in the field of medical devices. As an illustrative, non-limiting example, the catheter may have a braided configuration, such as the catheter associated with product number CXI-4.0-35-150-P-NS-0 manufactured by Cook Inc., which is available as of the filing date of this application.

Various aspects of access needles are described in the present disclosure. The access needles may be made from any suitable material(s) known in the art. In some aspects, the access needle comprises a plastic and/or a polymeric material. In other aspects, the access needle comprises a metal, such as stainless steel. In additional aspects, the access needle comprises any combination of a metal, a plastic, and a polymeric material.

Figure 1:
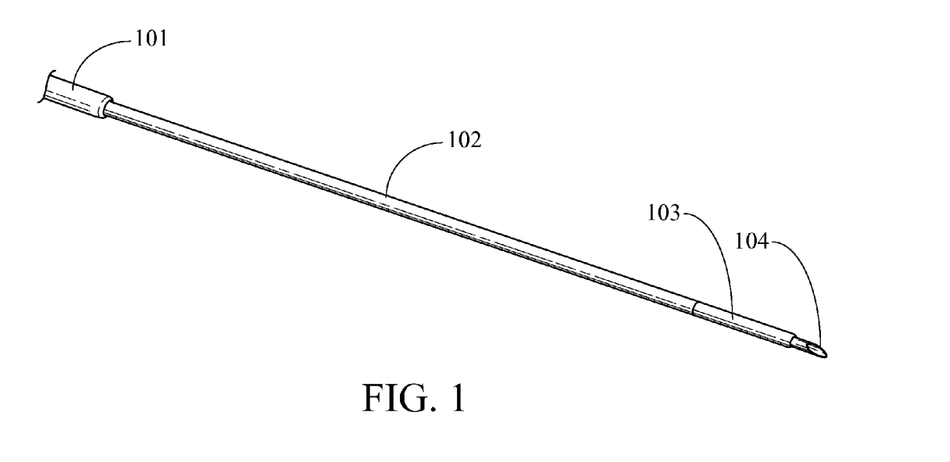
FIG. 1 depicts an aspect of the presently disclosed access needle.

With reference to FIG. 1, the access needle may include a handle (not shown) operatively connected to a proximal end of an elongate flexible cannula (102). In certain embodiments, the handle may be configured in a manner disclosed in U.S. Pat. No. 6,976,955 to Hardin, et al., which is incorporated herein by reference, while in other embodiments, the handle may be constructed in any manner appropriate for a biopsy needle (noting that the particular handle structure is not presently claimed and a variety of handle designs may readily be practiced by those having skill in the art of medical biopsy needle design and use). The cannula (102) includes a lumen extending from its proximal end to its distal end. In certain aspects, the distal end of the cannula can be configured to include an echogenic tip (103). In certain embodiments, a protective sheath (101) may surround the exterior of the cannula and a removable stylet may be placed within the lumen of the cannula (102). The stylet may include a piercing tip (104), configured for penetrating through an occlusion. A piercing tip includes any beveled, pointed, or otherwise configured tip known in the art to be effective for piercing and/or penetrating tissue. The piercing tip (104) may be solid or hollow.

The flexibility of at least a portion of the cannula provides pushability and trackability sufficient to allow navigation through a body lumen or other passage without significant risk of crimping or otherwise occluding the lumen. In an aspect, the cannula can be a plastic material comprising, for example, a polyimide, a polyether block amide (PEBA), PEBAX, poly-ether-ether-ketone (PEEK), ePTFE, PTFE, thermoplastic polyurethane (TPU), or PET. It will be appreciated that other polymeric materials including polymers with braided construction and/or with metallic components, such as stainless steel, may also be used within the scope of this disclosure.

In certain aspects, the distal end of the cannula may include an echogenic tip. In some aspects, the distal end of the cannula may be constructed from, or coated with, an echogenic polymer. In other aspects, the distal end of the cannula may be made echogenic by providing dimples, divots, etc., on its exterior surface. The dimples can reflect ultrasound waves sufficient to provide an image from, for example, an endoscopic ultrasound. Regardless of whether the distal end of the cannula is dimpled, coated with, or constructed from, an echogenic polymer, it will present an ultrasound-visualizable member that can provide location and navigation data.

The pushability and trackability of the cannula may be further enhanced by the placement of a stylet within its lumen. Once the distal end of the cannula and stylet arrive at the target site within the patient's body and a puncture is made, the stylet can be removed, thereby creating an access channel through the lumen of the cannula into the lesion. The soft cannula tip allows a coated wire guide to be inserted through the cannula lumen without stripping the coating from the wire.

The stylet may be constructed of an alloy, such as a nickel-titanium alloy, including a shape-memory alloy, stainless steel, steel NiTi, or it may be constructed of a polymer, such as PEEK. The distal end of the stylet may include a beveled tip, which may be beveled in a lancet configuration or any number of other beveled configurations configured for effectively piercing tissue. The tip of the stylet can be hollow or solid.

Figure 2:
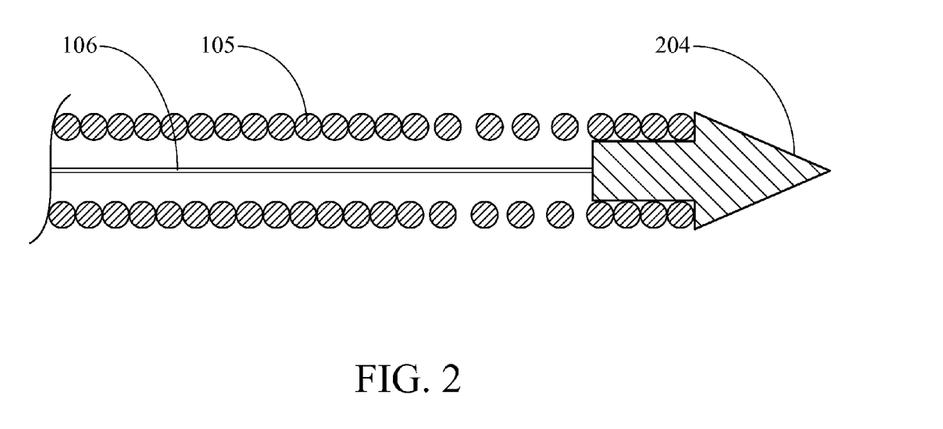
FIG. 2 depicts a longitudinal section of a coiled wire embodiment of a stylet.
Figure 3:
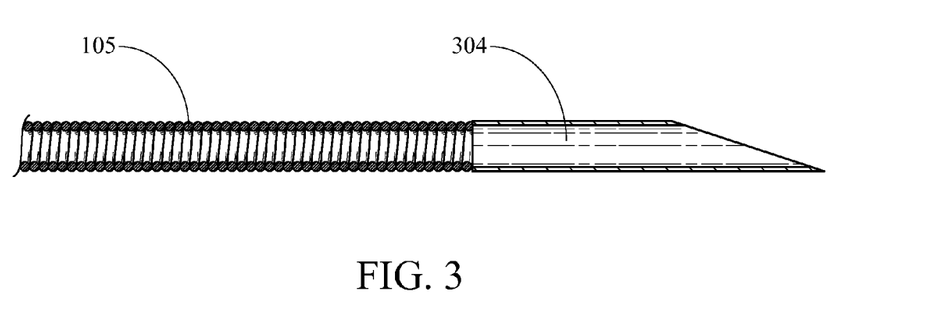
FIG. 3 depicts a longitudinal section of a coiled wire embodiment of a stylet.

With respect to FIGS. 2 and 3, in certain aspects of the present disclosure, a stylet (105) is provided in the form of a coiled wire. Such a coiled wire stylet (105) differs from a typical stylet configuration. A single wire or multiple wire braid/coil may be used. A support mandrel or drive wire (106) could also be provided within the lumen of the coiled wire stylet (105) to add strength. This type of stylet has numerous advantages over prior art stylets, which generally consist of a solid wire occupying the entire lumen of the cannula.

For example, the presently disclosed coiled wire stylet provides increased flexibility. The access needle is often used in a very contorted and convoluted manner. Thus, using the presently disclosed flexible, coiled wire stylet would allow for greater ease of use in these contorted and convoluted environments such as, for example, tortuous body lumens (e.g. blood vessels), passage through a duodenoscope into a patient's biliary tree, or other uses requiring a high degree of flexibility to reach a target site. As used herein, the terms "flexible" and "flexible body length" are defined and will be understood by those in the art to mean non-rigid, yet maintaining sufficient linear integrity to be pushable and trackable in a generally predictable guided manner through a needle cannula lumen, a gastric endoscope working channel, a tortious body lumen, or any other lumen or track. As such, the presently disclosed embodiments provide advantages over prior stylets (e.g. columnar and longitudinal needle support), while including further advantages described herein.

A medical professional will need to attempt to locate the distal end of the cannula as this end is navigating through the body to the target site (e.g., by visualization of the tip's location and orientation). It is desirable to keep the stylet in place during navigation and thus, the stylet will need to be constructed in a manner that will allow contrast fluid to pass through the cannula lumen. The presently disclosed coiled wire stylet (105) will allow for passage of the contrast fluid through the lumen of the cannula, and even through the lumen of the coiled wire stylet, so long as the drive wire (106), if used, does not sufficiently fill the lumen of the coiled wire stylet (105). If a prior art solid wire stylet were used and the outer diameter of the stylet was essentially equal to the inner diameter of the cannula lumen, injecting contrast fluid through the cannula lumen would not be possible or, at best, it would take a substantial period of time for the contrast fluid to flow through the cannula lumen and out the distal end where it could be detected. This feature is desirable so that fluoroscopic visualization can be done with a minimal time exposure (in keeping with best practices geared to minimize patient and treating personnel exposure to the radiation used during fluoroscopy).

However, by using the presently disclosed coiled wire stylet, contrast fluid can easily be injected into a port in the handle and freely flow to the proximal end of the cannula, through the lumen of the cannula and/or the lumen of the coiled wire stylet, and out the distal end of the cannula. If the tip of the stylet is hollow (see reference numeral 304 in FIG. 3), the contrast fluid can freely flow therethrough. If the distal end of the stylet is solid (see reference numeral 204 in FIG. 2), the contrast fluid would freely flow through the cannula or stylet lumen until it reached the solid stylet tip. However, the solid stylet tip could be of minimal length, potentially as short as about 5 mm in length, and it would not form a liquid-tight seal with the distal end of the cannula. Thus, the contrast fluid could leach out of the distal end of the cannula lumen. Suitable lengths for the stylet tip could be anywhere from about 5 mm to about 50 mm. Also, if the tip of the stylet is solid, the pitch of the coil at the distal end of the coiled wire can be increased (see distal end of stylet (105) shown in FIG. 2) to allow for passage of the contrast fluid out of the stylet lumen and past the solid tip at the distal end of the cannula.

If the tip of the stylet is hollow, the tip can be welded to the coiled wire. If the tip of the stylet is solid, it can also be welded to the coiled wire. Even further, if the tip of the stylet is solid, a drive wire (106) can be passed through the lumen of the coiled wire and the distal end of the drive wire can be welded to the proximal end of the stylet tip.

With reference to FIGS. 4, 5, 5A, and 6, a multiple wire stylet (205) may be used in accordance with the disclosed access needle. In this aspect, the stylet can comprise a plurality of wire strands (205). For example, the stylet can comprise two wire strands, three wire strands, four wire strands, five wire strands, six wire strands, seven wire strands, etc. The present disclosure is intended to cover a stylet comprising any number of wire strands.

Figure 4:
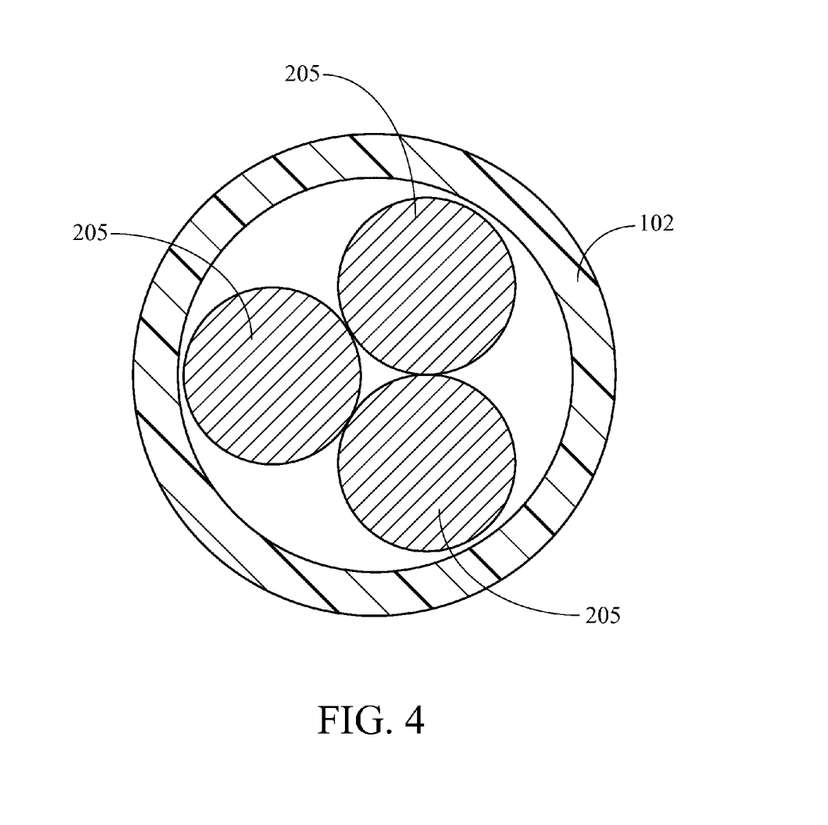
FIG. 4 depicts a transverse section of an embodiment of a multiple wire strand stylet.
Figure 5:
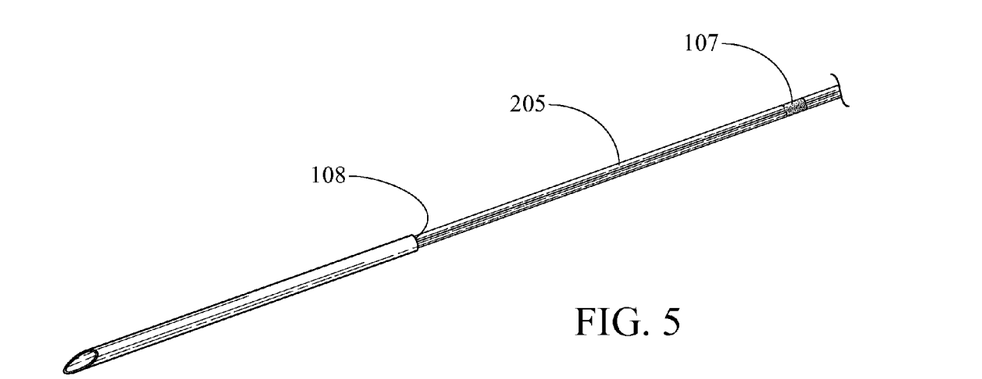
FIG. 5 depicts an aspect of a multiple wire strand stylet.
Figure 5A:
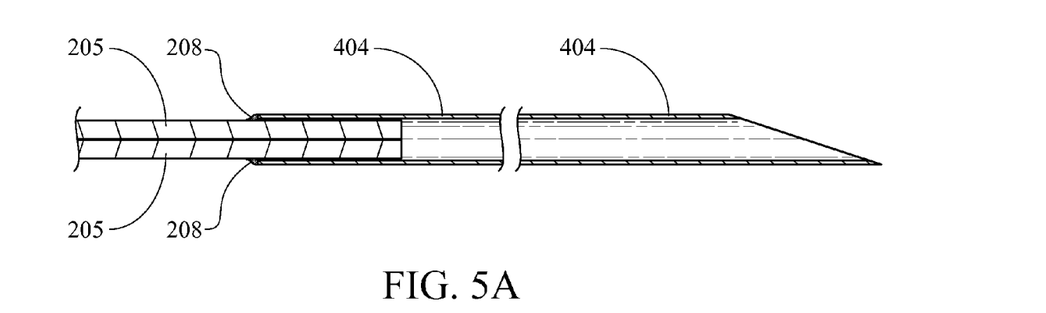
FIG. 5A depicts an aspect of a multiple wire strand stylet with cross-hatching showing attachment to a piercing tip.
Figure 6:
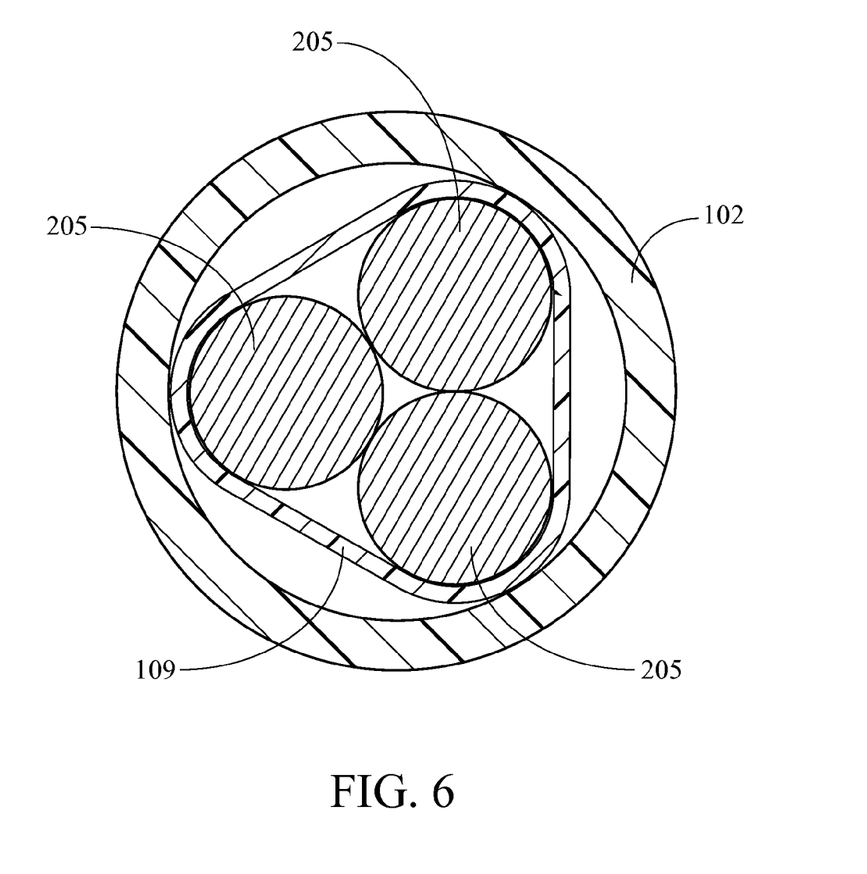
FIG. 6 depicts a transverse section of an embodiment of a multiple wire strand stylet.

As can be most clearly seen in FIGS. 4 and 6, in one particular aspect, the stylet may comprise three wire strands. Each wire strand can be made from the same materials mentioned in connection with the previously described coiled wire stylet. Each wire strand can be joined by welding, soldering, or the like, to a cannula with a sharp tip (see reference numeral 108 in FIG. 5 or 208 in FIG. 5A). The tip of the cannula can be hollow or it can be solid. The stylet can occupy a space from the proximal end of the cannula to its distal end. With such a configuration, the stylet does not substantially occupy the entire lumen of the cannula, thereby allowing for the passage of contrast fluid through the cannula lumen. As can be seen in, for example, FIG. 4, the multiple wire strand stylet leaves empty space in the cannula lumen where contrast fluid can freely flow.

The distal end of one or more of the wire strands of the multiple wire stylet may be joined to a hollow tip or a solid tip by welding, soldering, or the like. An adhesive may also be used. In one embodiment as shown in FIG. 5A, at the distal end of the stylet, each of the plurality of wire strands (205) passes into the inner diameter of the stylet tip (404). A weld or solder joint (208) may then be formed at the proximal end of the stylet tip, thereby attaching the stylet to the tip. In some embodiments, attachment of the wire strands to the cannula may still allow space for contrast fluid to pass through the stylet tip and in other embodiments, the joining of the wire strands to the tip may seal off the proximal end of the tip, meaning that the contrast fluid will leach out around tip of the stylet to emerge from the catheter.

Moreover, with reference to FIG. 5, the multiple wires can be joined together (107) by soldering or welding at certain portions of the stylet body for further reinforcement. When the access needle is being navigated through an endoscope, it may travel through tortuous positions while en route to the target site. Since the stylet does not occupy the entire lumen of the cannula, it may tend to push back into the cannula lumen as opposed to puncturing the target. However, if the wire strands were joined at certain locations along the stylet body, this would add further reinforcement and strength and prohibit the stylet strands from pushing back into the cannula lumen. Similarly, the wire strands preferably will be sized to the diameter of the cannula lumen, but by using multiple wire strands as opposed to a single solid wire, there will be sufficient spaces where a contrast fluid can pass (see FIGS. 4 and 6).

When joining multiple wire strands together along the body of the stylet, heat shrink tubing can be used (see reference numeral 109 in FIG. 6) as well as soldering, welding, and the like. The entire length of the multiple wire strand stylet can be joined together or, alternatively, the multiple wire strands can be joined periodically along the body of the stylet as previously described. In some embodiments, the multiple wire strands may be joined periodically at repeating intervals along the length of the wire strands. The intervals may be any length, such as intervals of about 1 inch to intervals of about 20 inches. For example, along the length of the multiple wire strands, the strands may be joined together at an interval of about every 12 inches or at an interval within the range of about every 8 inches to about every 16 inches.

At the proximal end of the presently disclosed access needle, the cannula can be connected to a handle/dual port luer adaptor. Contrast fluid can be injected through a side port of the luer adaptor and can freely flow past the stylet, whether it is a coiled wire stylet or a multiple wire stylet, through the cannula lumen and in some aspects, through the stylet lumen, and out of the distal end of the cannula past the stylet tip. Fluoroscopy can then be used to determine the location of the contrast fluid and thus, the location of the distal end of the cannula. Unless the stylet tip is hollow, the longer the tip of the stylet, the more it will impede the flow of contrast fluid, thereby increasing the period of time necessary for leaching to occur. As such, the stylet tip should be kept reasonably short in length, such as from about 5 mm to about 50 mm, from about 5 mm to about 25 mm, from about 5 mm to about 15 mm, or from about 5 mm to about 10 mm.

It can thus be appreciated that all aspects of the presently disclosed stylets will allow for efficient passage of contrast fluid through the lumen of the cannula and some aspects allow for efficient passage of contrast fluid through the lumen of the stylet. Contrast fluid can be highly viscous and thus, sufficient space is needed in the cannula lumen, which can be difficult to achieve due to the stylet being located therein. However, all aspects of the presently disclosed stylets allow sufficient space for the contrast fluid to pass. That is, all of the presently disclosed stylets can have flexible body lengths extending proximally from the piercing tip to the handle, whereby the flexible body of the stylet does not sufficiently occupy the entire lumen of the cannula such that a contrast fluid can effectively pass through the lumen of the cannula. In order for a stylet to not sufficiently occupy a lumen of a cannula, there must be enough unoccupied space in the cannula lumen for contrast fluid to pass unimpeded, at least until the fluid arrives at the stylet tip.

With reference to FIGS. 2 and 3, it can be seen that if contrast fluid were injected into a cannula lumen containing either of these stylets, there would be a large amount of unoccupied space within the cannula lumen where the contrast fluid could flow. For example, the contrast fluid could freely flow down the center of the lumen in the stylet. With reference to FIG. 4, it can easily be seen that this embodiment of the stylet does not sufficiently occupy the entire lumen of the cannula thereby allowing a contrast fluid to effectively pass through the lumen of the cannula. This figure shows a stylet comprising three wire strands. As can be seen in the figure, there is sufficient unoccupied space within the cannula lumen where a contrast fluid could freely pass.

In an attempt to quantify the amount of free space within the cannula lumen for the contrast fluid to pass, one could determine, at least with reference to FIGS. 2, 3, 4, and 6, that a cross section of the cannula lumen, when containing one of the presently disclosed stylets, is about 70% to about 10% unoccupied by the stylet. In certain aspects, the cannula lumen may be from about 20% to about 50% unoccupied. Thus, in all aspects disclosed herein, it can be appreciated that the flexible body of the stylet provides a path of fluid communication through the entire lumen of the cannula such that a contrast fluid can effectively pass through the lumen of the cannula. Alternatively, it can be said that since the flexible body of the stylet does not sufficiently occupy the entire lumen of the cannula, the flexible body of the stylet provides a path of fluid communication through the entire lumen of the cannula such that a contrast fluid can effectively pass through the lumen of the cannula.

In contrast to the presently disclosed stylets, it should be appreciated that a solid wire prior art stylet would sufficiently occupy the entire lumen of the cannula such that a contrast fluid could not effectively pass through the lumen of the cannula. Thus, the prior art stylets would not provide a path of fluid communication through the lumen of the stylet. With a solid wire stylet having a diameter essentially the same as the diameter of the cannula lumen, only about 1% to about, at most, 5%, and probably less, of the cannula lumen would be unoccupied by the stylet. This would seriously impede the flow of contrast fluid through the lumen. While it may be possible to inject contrast fluid into a cannula having a prior art solid wire stylet, the amount of time one would need to wait for the fluid to travel the length of the cannula would make the procedure impracticable.

Although certain aspects of the presently disclosed stylets have a solid tip that can, similarly to the prior art solid wire stylets, have diameters that are almost equal to the diameter of the cannula lumen, these tips are very short, potentially about 5 mm in length, so the amount of time one would need to wait for the contrast fluid to pass by such a short distance would be minimal.

Suitable contrast fluid is known in the art and the presently disclosed device is not particularly limited to any type of contrast fluid. Telebrix® is one illustrative example of a type of contrast fluid that can be used in connection with the presently disclosed access needle.

Methods of placing a cannula at a target location within the body of a patient are also disclosed herein. In one aspect, a target site within the body of a patient is visualized with an ultrasound endoscope. The presently disclosed access needle can be inserted into the ultrasound endoscope and attached to the scope. The handle of the access needle can be advanced to puncture the distal end of the cannula/stylet assembly into the target site within the body of the patient. With the stylet still in place in the lumen of the cannula, contrast fluid can be injected through a port in the handle. The contrast fluid can travel through the cannula lumen and, as previously described in connection with certain embodiments, through the lumen of the stylet. The contrast fluid will exit the distal end of the cannula and a medical professional operating the device will be able to fluoroscopically confirm the anatomical location of the distal end of the cannula prior to removal of the stylet. Once confirmation is received that the distal end of the cannula is at the correct location, the stylet may be removed. In accordance with the methods disclosed herein, either the coiled wire stylet or the multiple wire strand stylet can be used.

Upon removal of the stylet, the cannula will be left in place with its distal end at the target site. The next steps of the method depend upon the needs of the medical professional and the patient. For example, a syringe can be connected to the handle of the access needle to aspirate fluid from the target location. As an additional illustrative example, a wire guide can be passed through the cannula lumen into the target site within the patient's body. The handle of the access needle can then be retracted to bring the needle back into the sheath which surrounds the cannula. The device can then be removed from the endoscope, leaving the wire guide in place for further access to the target site.

All of the devices and methods disclosed and claimed herein can be made and executed without undue experimentation in light of the present disclosure. While this disclosure may pertain to many different aspects or embodiments, there are described in detail herein specific preferred embodiments of the invention. The present disclosure is an exemplification of the principles of the invention and is not intended to limit the invention to the particular embodiments or aspects illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. An access needle comprising:
    an elongate hollow cannula having a proximal end, a distal end, and a lumen extending therebetween; and
    a stylet removably disposed within the lumen of the cannula, the stylet comprising:
        a hollow piercing tip disposed at a distal end of the stylet; and
        a flexible body length comprising a plurality of wire strands, said wire strands contacting each other and being oriented both generally parallel with each other and with a central longitudinal axis of the stylet extending proximally from the piercing tip toward the proximal end, whereby an outer boundary of the flexible body of the stylet is sized to an inner diameter of the lumen of the cannula but the flexible body occupies less than an entire cross-sectional volume of the lumen and thereby provides a path of fluid communication through the entire lumen of the cannula such that a contrast fluid can effectively pass through the lumen of the cannula in contact with the cannula lumen, longitudinally between and around wire strands of the stylet, and through an inside of the hollow piercing tip while the stylet is disposed within the lumen of the cannula and contacts an inward-facing surface of the cannula that defines the lumen of the cannula between the proximal end and the distal end of the cannula.

2. The access needle of claim 1, wherein the stylet comprises a coiled wire.

3. The access needle of claim 1, wherein the plurality of wire strands comprises three wire strands each of which contacts the other two strands, and further wherein the outer boundary sized to the inner diameter of the lumen of the cannula provides said outer boundary maintaining longitudinal contact with the inner diameter of the lumen of the cannula.

4. The access needle of claim 3, wherein the three wire strands are joined together along the body of the stylet in one or more locations.

5. The access needle of claim 1, wherein the hollow piercing tip comprises stainless steel.

6. The access needle of claim 1, wherein a distal end of each wire strand comprising the plurality of wire strands is connected in direct contact with a proximal end of the piercing tip.

7. The access needle of claim 1, wherein the plurality of wire strands is joined together along the body of the stylet in one or more locations.

8. The access needle of claim 1, wherein the distal end of the elongate hollow cannula comprises a dimpled surface configured to enhance echogenicity.

9. A method of introducing a cannula to a target location within a body of a patient through an endoscope comprising:
loading the distal end of the access needle of claim 1 into a lumen of the endoscope;
puncturing the distal end of the access needle into the target location;
directing contrast fluid to flow through the cannula lumen and exit the distal end of the cannula through and/or around the stylet while the stylet is disposed within the lumen and is contacting an inward-facing lumen surface of the cannula between the proximal end and the distal end of the access needle;
fluoroscopically visualizing the body of the patient to determine a location of the contrast fluid;
confirming by the location of the contrast fluid that the distal end of the cannula is at the target location;
withdrawing the stylet; and
leaving the cannula in place with the distal end of the cannula at the target location.

10. The method of claim 9, further comprising steps of connecting a syringe to the handle of the access needle and aspirating fluid from the target location.

11. The method of claim 9, further comprising a step of passing a wire guide through the cannula lumen into the target location.

12. The method of claim 11, further comprising steps of retracting the handle of the access needle, withdrawing the needle into the sheath, and removing the access needle from the endoscope, thereby leaving the wire guide in place for further access to the target location.

13. The method of claim 9, wherein the stylet comprises a coiled wire.

14. The method of claim 9, wherein the plurality of wire strands comprises three wire strands each of which contacts the other two strands, and further wherein the outer boundary sized to the inner diameter of the lumen of the cannula provides said outer boundary maintaining longitudinal contact with the inner diameter of the lumen of the cannula.

15. The method of claim 14, wherein each of the plurality of wire strands is joined together with other(s) of the plurality of wire strands along the body of the stylet.

16. The method of claim 14, wherein a distal end of each wire strand comprising the plurality of wire strands in direct contact with a proximal end of the piercing tip.

17. An access needle comprising:
an elongate hollow cannula having a proximal end, a distal end, and a lumen extending therebetween; and
a stylet removably disposed within the lumen of the cannula, the stylet comprising:
a hollow piercing tip at a distal end of the stylet; and
a flexible body length extending proximally from the piercing tip toward the proximal end, whereby the flexible body of the stylet comprises a plurality of wires generally longitudinally parallel with each other and with a central longitudinal axis, which stylet provides a path of fluid communication through the entire lumen of the cannula such that a contrast fluid can effectively pass through the lumen of the cannula between the wires and through the hollow piercing tip while the stylet is disposed within the lumen between the proximal end and the distal end and contacts an inward-facing surface of the cannula defining the lumen, wherein a distal end of each wire is connected in direct contact with a proximal end of the hollow piercing tip.

18. The access needle of claim 17, wherein the plurality of wires comprises three wire strands that are joined together periodically along the flexible body length of the stylet and further wherein the hollow piercing tip is beveled and comprises stainless steel.

\* \* \* \* \*